United States Patent
Melsky

(10) Patent No.: US 11,246,476 B2
(45) Date of Patent: Feb. 15, 2022

(54) METHOD FOR VISUALIZING TISSUE WITH AN ICG DYE COMPOSITION DURING ABLATION PROCEDURES

(71) Applicant: CardioFocus, Inc., Marlborough, MA (US)

(72) Inventor: Gerald Melsky, Lexington, MA (US)

(73) Assignee: CARDIOFOCUS, INC., Marlborough, MA (US)

(*) Notice: Subject to any disclaimer, the term of this patent is extended or adjusted under 35 U.S.C. 154(b) by 260 days.

(21) Appl. No.: 16/259,483

(22) Filed: Jan. 28, 2019

(65) Prior Publication Data

US 2019/0150718 A1 May 23, 2019

Related U.S. Application Data

(62) Division of application No. 14/697,065, filed on Apr. 27, 2015, now abandoned.

(Continued)

(51) Int. Cl.
*A61B 1/04* (2006.01)
*A61B 1/06* (2006.01)
(Continued)

(52) U.S. Cl.
CPC .......... *A61B 1/043* (2013.01); *A61B 1/0638* (2013.01); *A61B 5/0036* (2018.08);
(Continued)

(58) Field of Classification Search
CPC ..... A61B 1/043; A61B 1/0005; A61B 5/0071; A61B 5/0036; A61B 5/0084;
(Continued)

(56) References Cited

U.S. PATENT DOCUMENTS

| 3,417,745 A | 12/1968 | Sheldon |
| 3,821,510 A | 6/1974 | Muncheryan |

(Continued)

FOREIGN PATENT DOCUMENTS

| DE | 94117543 | 11/1994 |
| EP | 0214712 | 3/1987 |

(Continued)

OTHER PUBLICATIONS

Bredikis, J. et al. "Laser Destruction of the Atrioventricular Bundle Using the Cardiac Endoscope" Kardiologiia, Aug. 1988, 28(8): 94-96.

(Continued)

*Primary Examiner* — Alexandra L Newton
*Assistant Examiner* — Jae Woo
(74) *Attorney, Agent, or Firm* — Leason Ellis LLP

(57) ABSTRACT

A system is provided for identifying the sufficiency of lesions formed during a tissue ablation procedure. The system and method include administering an ICG composition to the patient and forming one or more lesions at a surgical site. The method further includes applying energy of a type and in an amount sufficient to cause ICG in the patient to fluoresce. An image of the tissue and lesion at the surgical site is obtained while the ICG fluoresces. The lesion is distinguished from surrounding de novo tissue based on areas of fluorescence to allow a user to evaluate the quality of the lesion.

10 Claims, 9 Drawing Sheets

Related U.S. Application Data

(60) Provisional application No. 61/985,142, filed on Apr. 28, 2014.

(51) Int. Cl.
  *A61B 5/00* (2006.01)
  *A61B 18/20* (2006.01)
  *A61B 18/00* (2006.01)
  *A61B 17/00* (2006.01)
  *A61B 1/00* (2006.01)
  *A61B 90/00* (2016.01)
  *A61B 90/30* (2016.01)

(52) U.S. Cl.
  CPC .......... *A61B 5/0071* (2013.01); *A61B 5/0084* (2013.01); *A61B 18/20* (2013.01); *A61B 1/0005* (2013.01); *A61B 90/30* (2016.02); *A61B 90/361* (2016.02); *A61B 2017/00061* (2013.01); *A61B 2018/00577* (2013.01); *A61B 2018/00982* (2013.01); *A61B 2090/373* (2016.02); *A61B 2090/376* (2016.02); *A61B 2090/3941* (2016.02)

(58) Field of Classification Search
  CPC ............ A61B 5/4836; A61B 2090/373; A61B 2090/3941; A61B 2017/0061
  See application file for complete search history.

(56) References Cited

U.S. PATENT DOCUMENTS

| | | |
|---|---|---|
| 4,224,929 A | 9/1980 | Furihata et al. |
| 4,233,493 A | 11/1980 | Nath et al. |
| 4,273,109 A | 6/1981 | Enderby |
| 4,336,809 A * | 6/1982 | Clark .................. A61B 5/0084 600/478 |
| 4,445,892 A | 12/1984 | Hussein et al. |
| 4,585,298 A | 4/1986 | Mori et al. |
| 4,625,724 A | 12/1986 | Suzuki et al. |
| 4,660,925 A | 4/1987 | McCaughan, Jr. |
| 4,701,166 A | 10/1987 | Groshong et al. |
| 4,718,417 A | 1/1988 | Kittrell et al. |
| 4,770,653 A | 9/1988 | Shturman |
| 4,781,681 A | 11/1988 | Sharrow et al. |
| 4,819,632 A | 4/1989 | Davies et al. |
| 4,842,390 A | 6/1989 | Sottini et al. |
| 4,852,567 A | 8/1989 | Sinofsky |
| 4,860,743 A | 8/1989 | Abela |
| 4,862,886 A | 9/1989 | Clarke et al. |
| 4,878,492 A | 11/1989 | Sinofsky et al. |
| 4,878,725 A | 11/1989 | Hessel et al. |
| 4,913,142 A | 4/1990 | Kittrell et al. |
| 4,961,738 A | 10/1990 | Mackin |
| 5,026,367 A | 6/1991 | Leckrone et al. |
| 5,030,201 A | 7/1991 | Palestrant |
| 5,053,033 A | 10/1991 | Clarke |
| 5,071,417 A | 12/1991 | Sinofsky |
| 5,078,681 A | 1/1992 | Kawashima et al. |
| 5,109,859 A | 5/1992 | Jenkins |
| 5,125,925 A | 6/1992 | Lundahl |
| 5,133,709 A | 7/1992 | Prince |
| 5,140,987 A | 8/1992 | Schuger et al. |
| 5,151,096 A | 9/1992 | Khoury |
| 5,151,097 A | 9/1992 | Daikuzono et al. |
| 5,163,935 A | 11/1992 | Black et al. |
| 5,090,959 A | 12/1992 | Samson et al. |
| 5,169,395 A | 12/1992 | Narciso, Jr. |
| 5,188,632 A | 2/1993 | Goldenberg |
| 5,188,634 A | 2/1993 | Hussein et al. |
| 5,190,538 A | 3/1993 | Hussein et al. |
| 5,196,005 A | 3/1993 | Doiron et al. |
| 5,207,699 A | 5/1993 | Coe |
| 5,209,748 A | 5/1993 | Daikuzono et al. |
| 5,219,346 A | 6/1993 | Wagnieres et al. |
| 5,242,438 A | 9/1993 | Saadatmanesh et al. |
| 5,261,904 A | 11/1993 | Baker et al. |
| 5,269,777 A | 12/1993 | Doiron et al. |
| RE34,544 E | 2/1994 | Spears |
| 5,318,024 A | 6/1994 | Kittrell et al. |
| 5,330,465 A | 7/1994 | Doiron et al. |
| 5,337,381 A | 8/1994 | Biswas et al. |
| 5,344,419 A | 9/1994 | Spears |
| 5,350,375 A | 9/1994 | Deckelbaum et al. |
| 5,363,458 A | 11/1994 | Pan et al. |
| 5,368,564 A | 11/1994 | Savage |
| 5,374,953 A | 12/1994 | Sasaki et al. |
| 5,380,316 A | 1/1995 | Aita et al. |
| 5,380,317 A | 1/1995 | Everett et al. |
| 5,395,362 A | 3/1995 | Sacharoff et al. |
| 5,401,270 A | 3/1995 | Muller et al. |
| 5,409,483 A | 4/1995 | Campbell et al. |
| 5,417,653 A | 5/1995 | Sahota et al. |
| 5,418,649 A | 5/1995 | Igarashi et al. |
| 5,423,805 A | 6/1995 | Brucker et al. |
| 5,427,119 A | 6/1995 | Swartz et al. |
| 5,431,647 A | 7/1995 | Purcell, Jr. et al. |
| 5,437,660 A | 8/1995 | Johnson et al. |
| 5,441,497 A | 8/1995 | Narciso, Jr. |
| 5,445,608 A | 8/1995 | Chen et al. |
| 5,464,404 A | 11/1995 | Abela et al. |
| 5,482,037 A | 1/1996 | Borghi et al. |
| 5,496,305 A | 3/1996 | Kittrell et al. |
| 5,497,774 A | 3/1996 | Swartz et al. |
| 5,507,725 A | 4/1996 | Savage et al. |
| 5,531,664 A | 7/1996 | Adachi et al. |
| 5,536,265 A | 7/1996 | van den Bergh et al. |
| 5,575,766 A | 11/1996 | Swartz et al. |
| 5,605,162 A | 2/1997 | Mirzaee et al. |
| 5,613,965 A | 3/1997 | Muller |
| 5,630,837 A | 5/1997 | Crowley |
| 5,643,253 A | 7/1997 | Baxter et al. |
| 5,649,923 A | 7/1997 | Gregory et al. |
| 5,662,712 A | 9/1997 | Pathak et al. |
| 5,678,550 A | 10/1997 | Bassen et al. |
| 5,680,860 A | 10/1997 | Imran |
| 5,690,611 A | 11/1997 | Swartz et al. |
| 5,693,043 A | 12/1997 | Kittrell et al. |
| 5,700,243 A | 12/1997 | Narciso, Jr. |
| 5,702,438 A | 12/1997 | Avitall |
| 5,722,401 A | 3/1998 | Pietroski et al. |
| 5,725,522 A | 3/1998 | Sinofsky |
| 5,741,249 A | 4/1998 | Moss et al. |
| 5,759,619 A | 6/1998 | Jin et al. |
| 5,769,843 A | 6/1998 | Abela et al. |
| 5,772,590 A | 6/1998 | Webster, Jr. |
| 5,773,835 A * | 6/1998 | Sinofsky .............. A61B 5/0071 250/462.1 |
| 5,775,327 A * | 7/1998 | Randolph ......... A61M 25/0054 600/374 |
| 5,779,646 A | 7/1998 | Koblish et al. |
| 5,782,239 A | 7/1998 | Webster, Jr. |
| 5,782,899 A | 7/1998 | Imran |
| 5,800,482 A | 9/1998 | Pomeranz et al. |
| 5,807,395 A | 9/1998 | Mulier et al. |
| 5,823,955 A | 10/1998 | Kuck et al. |
| 5,824,005 A | 10/1998 | Motamedi et al. |
| 5,830,209 A | 11/1998 | Savage et al. |
| 5,833,682 A | 11/1998 | Amplatz et al. |
| 5,843,073 A | 12/1998 | Sinofsky |
| 5,845,646 A * | 12/1998 | Lemelson ...... A61B 17/320758 128/899 |
| 5,860,974 A | 1/1999 | Abele |
| 5,885,278 A | 3/1999 | Fleischman |
| 5,891,133 A | 4/1999 | Murphy-Chutorian |
| 5,891,134 A | 4/1999 | Goble et al. |
| 5,904,651 A | 5/1999 | Swanson et al. |
| 5,908,415 A | 6/1999 | Sinofsky |
| 5,908,448 A | 6/1999 | Roberts et al. |
| 5,931,834 A | 8/1999 | Murphy-Chutorian et al. |
| 5,938,660 A | 8/1999 | Swartz et al. |
| 5,947,959 A | 9/1999 | Sinofsky |
| 5,967,984 A | 10/1999 | Chu et al. |
| 5,971,983 A | 10/1999 | Lesh |

(56) References Cited

U.S. PATENT DOCUMENTS

| | | | |
|---|---|---|---|
| 5,995,875 A | 11/1999 | Blewett et al. | |
| 6,004,269 A | 12/1999 | Crowley et al. | |
| 6,012,457 A | 1/2000 | Lesh | |
| 6,024,740 A | 2/2000 | Lesh et al. | |
| 6,056,744 A | 5/2000 | Edwards | |
| 6,064,902 A | 5/2000 | Haissaguerre et al. | |
| 6,071,279 A | 6/2000 | Whayne et al. | |
| 6,071,281 A | 6/2000 | Burnside et al. | |
| 6,071,282 A | 6/2000 | Fleischman | |
| 6,071,302 A | 6/2000 | Sinofsky et al. | |
| 6,086,581 A | 7/2000 | Reynolds et al. | |
| 6,090,084 A | 7/2000 | Hassett et al. | |
| 6,099,514 A | 8/2000 | Sharkey et al. | |
| 6,102,905 A | 8/2000 | Baxter et al. | |
| 6,117,071 A | 9/2000 | Ito et al. | |
| 6,117,101 A | 9/2000 | Diederich et al. | |
| 6,120,496 A | 9/2000 | Whayne et al. | |
| 6,146,379 A | 11/2000 | Fleischman et al. | |
| 6,159,203 A | 12/2000 | Sinofsky | |
| 6,161,543 A * | 12/2000 | Cox | A61B 18/1492 128/898 |
| 6,164,283 A * | 12/2000 | Lesh | A61B 18/10 128/898 |
| 6,179,835 B1 | 1/2001 | Panescu et al. | |
| 6,214,002 B1 | 4/2001 | Fleischman et al. | |
| 6,217,510 B1 | 4/2001 | Ozawa et al. | |
| 6,235,025 B1 | 5/2001 | Swartz et al. | |
| 6,237,605 B1 | 5/2001 | Vaska et al. | |
| 6,240,231 B1 | 5/2001 | Ferrera et al. | |
| 6,245,064 B1 * | 6/2001 | Lesh | A61B 18/00 606/34 |
| 6,251,092 B1 | 6/2001 | Qin et al. | |
| 6,251,109 B1 | 6/2001 | Hassett et al. | |
| 6,254,599 B1 | 7/2001 | Lesh et al. | |
| 6,270,492 B1 | 8/2001 | Sinofsky | |
| 6,305,378 B1 | 10/2001 | Lesh | |
| 6,312,427 B1 | 11/2001 | Berube et al. | |
| 6,314,962 B1 | 11/2001 | Vaska et al. | |
| 6,325,797 B1 | 12/2001 | Stewart et al. | |
| 6,352,531 B1 | 3/2002 | O'Connor et al. | |
| 6,375,654 B1 | 4/2002 | Mcintyre | |
| 6,383,151 B1 * | 5/2002 | Diederich | A61B 18/00 601/2 |
| 6,394,949 B1 | 5/2002 | Crowley et al. | |
| 6,416,511 B1 | 7/2002 | Lesh et al. | |
| 6,423,055 B1 | 7/2002 | Farr et al. | |
| 6,423,058 B1 | 7/2002 | Edwards et al. | |
| 6,471,697 B1 | 10/2002 | Lesh | |
| 6,485,485 B1 | 11/2002 | Winston et al. | |
| 6,500,174 B1 | 12/2002 | Maguire et al. | |
| 6,502,576 B1 | 1/2003 | Lesh | |
| 6,503,247 B2 | 1/2003 | Swartz et al. | |
| 6,514,249 B1 | 2/2003 | Maguire et al. | |
| 6,522,933 B2 | 2/2003 | Nguyen | |
| 6,544,262 B2 | 4/2003 | Fleischman | |
| 6,547,780 B1 | 4/2003 | Sinofsky | |
| 6,554,794 B1 | 4/2003 | Mueller et al. | |
| 6,558,375 B1 | 5/2003 | Sinofsky et al. | |
| 6,562,020 B1 | 5/2003 | Constantz et al. | |
| 6,572,609 B1 | 6/2003 | Farr et al. | |
| 6,579,278 B1 | 6/2003 | Bencini | |
| 6,579,285 B2 | 6/2003 | Sinofsky | |
| 6,582,536 B2 | 6/2003 | Shimada | |
| 6,605,055 B1 | 8/2003 | Sinofsky | |
| 6,605,084 B2 | 8/2003 | Acker et al. | |
| 6,626,900 B1 | 9/2003 | Sinofsky et al. | |
| 6,635,054 B2 | 10/2003 | Fjield et al. | |
| 6,648,875 B2 | 11/2003 | Simpson et al. | |
| 6,669,655 B1 | 12/2003 | Acker et al. | |
| 6,676,656 B2 | 1/2004 | Sinofsky | |
| 6,679,873 B2 | 1/2004 | Rabiner et al. | |
| 6,702,780 B1 | 3/2004 | Gilboa et al. | |
| 6,771,996 B2 | 8/2004 | Bowe et al. | |
| 6,796,972 B1 | 9/2004 | Sinofsky et al. | |
| 6,896,673 B2 | 5/2005 | Hooven | |
| 6,907,298 B2 | 6/2005 | Smits et al. | |
| 6,916,306 B1 | 7/2005 | Jenkins et al. | |
| 6,932,809 B2 | 8/2005 | Sinofsky | |
| 6,942,657 B2 | 9/2005 | Sinofsky et al. | |
| 6,953,457 B2 | 10/2005 | Farr et al. | |
| 6,964,660 B2 | 11/2005 | Maguire et al. | |
| 6,997,924 B2 | 2/2006 | Schwartz et al. | |
| 7,137,395 B2 | 11/2006 | Fried et al. | |
| 7,207,984 B2 | 4/2007 | Farr et al. | |
| 7,357,796 B2 | 4/2008 | Farr et al. | |
| 7,935,108 B2 | 5/2011 | Baxter et al. | |
| 8,025,661 B2 | 9/2011 | Arnold et al. | |
| 8,444,639 B2 | 5/2013 | Arnold et al. | |
| 8,647,119 B1 | 2/2014 | Nagai | |
| 8,702,688 B2 * | 4/2014 | Melsky | A61B 18/24 606/14 |
| 9,775,497 B2 * | 10/2017 | Igarashi | A61B 1/04 |
| 10,219,742 B2 * | 3/2019 | Dvorsky | A61B 5/489 |
| 10,258,285 B2 * | 4/2019 | Hauck | A61B 34/30 |
| 2001/0030107 A1 | 10/2001 | Simpson | |
| 2002/0019627 A1 | 2/2002 | Maguire et al. | |
| 2002/0029062 A1 * | 3/2002 | Satake | A61M 25/10 606/194 |
| 2002/0065512 A1 | 5/2002 | Fjield et al. | |
| 2002/0091383 A1 | 7/2002 | Hooven | |
| 2002/0107511 A1 | 8/2002 | Collins et al. | |
| 2002/0115995 A1 | 8/2002 | Lesh et al. | |
| 2002/0120264 A1 | 8/2002 | Crowley et al. | |
| 2002/0173785 A1 * | 11/2002 | Spear | A61M 25/0668 606/41 |
| 2002/0183729 A1 | 12/2002 | Farr et al. | |
| 2002/0183739 A1 | 12/2002 | Long | |
| 2003/0050632 A1 | 3/2003 | Fjield et al. | |
| 2003/0065307 A1 | 4/2003 | Lesh | |
| 2003/0069620 A1 * | 4/2003 | Li | A61M 25/10 607/101 |
| 2003/0111085 A1 | 6/2003 | Lesh | |
| 2003/0120270 A1 | 6/2003 | Acker | |
| 2003/0144657 A1 | 7/2003 | Bowe et al. | |
| 2003/0158550 A1 | 8/2003 | Ganz et al. | |
| 2003/0171746 A1 | 9/2003 | Fleischman | |
| 2004/0006333 A1 | 1/2004 | Arnold et al. | |
| 2004/0054360 A1 | 3/2004 | Schwartz et al. | |
| 2004/0059397 A1 | 3/2004 | Sinofsky et al. | |
| 2004/0122290 A1 | 6/2004 | Irion et al. | |
| 2004/0186351 A1 * | 9/2004 | Imaizumi | A61B 5/0071 600/160 |
| 2005/0038419 A9 | 2/2005 | Arnold et al. | |
| 2005/0065504 A1 * | 3/2005 | Melsky | A61B 18/1482 606/16 |
| 2005/0222558 A1 | 10/2005 | Baxter et al. | |
| 2005/0234436 A1 | 10/2005 | Baxter et al. | |
| 2005/0288654 A1 | 12/2005 | Nieman et al. | |
| 2006/0253113 A1 | 11/2006 | Arnold et al. | |
| 2006/0268402 A1 * | 11/2006 | Eustergerling | H04N 5/332 359/386 |
| 2007/0078451 A1 | 4/2007 | Arnold et al. | |
| 2007/0087445 A1 * | 4/2007 | Tearney | G01N 21/6456 436/172 |
| 2008/0039746 A1 | 2/2008 | Hissong et al. | |
| 2008/0108870 A1 | 5/2008 | Wiita et al. | |
| 2008/0195088 A1 | 8/2008 | Farr et al. | |
| 2008/0306337 A1 * | 12/2008 | Livingston | A61B 5/0075 600/109 |
| 2009/0093728 A1 * | 4/2009 | Hyde | A61B 5/412 600/476 |
| 2009/0093807 A1 * | 4/2009 | Hyde | A61B 5/0071 606/34 |
| 2009/0177272 A1 * | 7/2009 | Abbate | A61F 2/95 623/1.42 |
| 2009/0221996 A1 | 9/2009 | Lesh et al. | |
| 2009/0221997 A1 | 9/2009 | Arnold et al. | |
| 2009/0275934 A1 | 11/2009 | Baxter et al. | |
| 2009/0299354 A1 * | 12/2009 | Melsky | A61B 18/245 606/16 |
| 2009/0326320 A1 * | 12/2009 | Sinofsky | A61B 1/07 600/109 |
| 2010/0247436 A1 | 9/2010 | Adair et al. | |

(56) References Cited

U.S. PATENT DOCUMENTS

| | | | |
|---|---|---|---|
| 2010/0280504 A1 | 11/2010 | Manzke et al. | |
| 2011/0082449 A1* | 4/2011 | Melsky | A61B 18/24 606/14 |
| 2011/0082450 A1* | 4/2011 | Melsky | A61B 18/24 606/14 |
| 2011/0082451 A1* | 4/2011 | Melsky | A61B 18/24 606/14 |
| 2011/0082452 A1* | 4/2011 | Melsky | A61B 18/24 606/15 |
| 2011/0158914 A1* | 6/2011 | Yamada | A61B 1/00009 424/9.6 |
| 2011/0245822 A1 | 10/2011 | Baxter et al. | |
| 2011/0245828 A1 | 10/2011 | Baxter et al. | |
| 2012/0150046 A1 | 6/2012 | Watson et al. | |
| 2012/0226166 A1 | 9/2012 | Saadat et al. | |
| 2012/0271299 A1 | 10/2012 | Whayne et al. | |
| 2013/0102862 A1 | 4/2013 | Mercader et al. | |
| 2013/0190741 A1 | 7/2013 | Moll et al. | |
| 2013/0190747 A1* | 7/2013 | Koblish | A61B 5/287 606/33 |
| 2013/0324797 A1* | 12/2013 | Igarashi | A61B 1/0684 600/109 |
| 2014/0350534 A1* | 11/2014 | Kircher | A61B 18/203 606/10 |
| 2015/0018807 A1* | 1/2015 | Kircher | A61B 5/7445 606/12 |
| 2015/0182118 A1* | 7/2015 | Bradbury | A61P 25/02 600/431 |
| 2015/0305604 A1* | 10/2015 | Melsky | A61B 1/0638 600/104 |
| 2016/0030022 A1* | 2/2016 | Sheth | A61B 1/043 600/424 |
| 2016/0038027 A1* | 2/2016 | Brzozowski | A61B 5/0036 600/431 |
| 2019/0099211 A1* | 4/2019 | Altmann | A61B 5/6852 |

FOREIGN PATENT DOCUMENTS

| | | |
|---|---|---|
| EP | 0292621 | 11/1988 |
| EP | 0292695 | 11/1988 |
| EP | 0299448 | 1/1989 |
| EP | 0311458 | 4/1989 |
| EP | 0437181 | 7/1991 |
| EP | 0437183 | 7/1991 |
| EP | 0439629 | 8/1991 |
| EP | 0598984 | 6/1994 |
| EP | 0792664 | 9/1997 |
| EP | 1072231 | 1/2001 |
| EP | 1331893 | 12/2004 |
| FR | 2798371 | 3/2001 |
| JP | 2003-210028 A | 7/2003 |
| JP | 2004-065076 A | 3/2004 |
| WO | WO 9217243 | 10/1992 |
| WO | WO 9306888 | 4/1993 |
| WO | WO 9319680 | 10/1993 |
| WO | WO 9325155 | 12/1993 |
| WO | WO 9417434 | 8/1994 |
| WO | WO 9426184 | 11/1994 |
| WO | WO 9607451 | 3/1996 |
| WO | WO 199634646 | 11/1996 |
| WO | WO 9640342 | 12/1996 |
| WO | WO 9737714 | 10/1997 |
| WO | WO 00/67656 | 1/2000 |
| WO | WO 00/67832 | 11/2000 |
| WO | WO 01/03599 A2 | 1/2001 |
| WO | WO 0113812 | 3/2001 |
| WO | WO 01/64123 | 9/2001 |
| WO | WO 02/096479 | 12/2002 |
| WO | WO 03090835 | 11/2003 |
| WO | WO 2004-110258 | 2/2004 |

OTHER PUBLICATIONS

Chevalier, P. et al. "Thoracoscopic Epicardial Radiofrequency Ablation for Vagal Atrial Fibrillation in Dogs" PACE, Jun. 1999, 22: 880-886.

Froelich, J. et al. "Evaluation of a Prototype Steerable Angioscopic Laser Catheter in a Canine Model: A Feasibility Study" Cardiovasc Intervent Radiol, Jul.-Aug. 1993 16: 235-238.

Fujimura, O. et al. "Direct In Vivo Visualization of Right Cardiac Anatomy by Fiberoptic Endoscopy" Angiology; Mar. 1995, 46 (3): 201-208.

Fujimura, O. et al. "Direct In Vivo Visualization of Right Cardiac Anatomy by Fiberoptic Endoscopy: Observation of Radiofrequency-Induced Acute Lesions Around the Ostium of the Coronary Sinus" European Heart J., Apr. 1994, 15: 534-540.

Gamble, W. and Innis, R. "Experimental Intracardiac Visualization" NEJM, Jun. 22, 1967, 276(25): 1397-1403.

Hirao, K. et al. Transcatheter Neodymium-Yttrium-Aluminum-Garnet Laser Coagulation of Canine Ventricle Using a Balloon-Tipped Cardioscope Jpn Circ J., Aug. 1997, 61: 695-703.

Keane, D. et al. "Pulmonary Vein Isolation for Atrial Fibrillation" Rev Cardiovasc Med., Fall 2002, 3(4): 167-175.

Kuo, C. et al. "In Vivo Angioscopic Visualization of Right Heart Structure in Dogs by Means of a Balloon-Tipped Fiberoptic Endoscope: Potential Role in Percutaneous Ablative Procedures." American Heart J., 1994, 127: 187-197. Accepted Jun. 1, 1993.

Nakagawa, H. et al. "Cardioscopic Catheter Ablation with Noncontact, Pulsed Nd:YAG Laser Using Saline Inflated Balloon Catheter," Presentation JACC Feb. 1998; 31: 118A-119A.

Obelienius, V. et al. "Transvenous Ablation of the Atrioventricular Conduction System by Laser Irradiation Under Endoscopic Control" Lasers in Surgery Medicine, Jun. 13, 1985, 5: 469-474.

Roggan, A., et al. "Optical Properties of Circulating Human Blood in the Wavelength Range 400-2400 nm" J Biomedical Optics, Jan. 1999, 4(1): 36-46.

Saliba, W. et al. "Circumferential Ultrasound Ablation for Pulmonary Vein Isolation: Analysis of Acute and Chronic Failures" J Cardiovascular Electrophysiology, Oct. 2002, 13(10): 957-961.

Shure, D. et al. "Identification of Pulmonary Emboli in the Dog: Comparison of Angioscopy and Perfusion Scanning" Circulation, Sep. 1981, 64(3): 618-621.

Shure, D., et al. "Fiberoptic Angioscopy: Role in the Diagnosis of Chronic Pulmonary Arterial Obstruction" Ann Int Med., Dec. 1985, 103: 844-850.

Tanabe, T. et al. "Cardiovascular Fiberoptic Endoscopy: Development and Clinical Application" Surgery, 1980, 87(4): 375-379. Accepted Jul. 20, 1989.

Tanaka, K. et al., "Endoscopy-Assisted Radiofrequency Ablation Around the Coronary Sinus Ostium in Dogs: Its Effects on Atrioventricular Nodal Properties and Ventricular Response During Atrial Fibrillation," Journal of Cardiovascular Electrophysiology, vol. 7, No. 11, Nov. 1996, pp. 1063-1073.

Uchida, Y. et al. "Fiberoptic Angioscopy of Cardiac Chambers, Valves, and Great Vessels Using a Guiding Balloon Catheter in Dogs." American Heart J., Jan. 20, 1998, 115(6): 1297-1302.

Uchida, Y. et al. "Percutaneous Pulmonary Angioscopy Using a Guiding Balloon Catheter" Clin. Cardiol., 1988, 11: 143-148, Sep. 14, 1987.

Vanermen, H. et al. "Minimally Invasive Video-Assisted Mitral Valve Surgery: From Port-Access Towards a Totally Endoscopic Procedure" J Card Surg., Jan.-Feb. 2000, 15: 51-60.

Yamamoto, N et al. "Nonfluoroscopic Guidance for Catheter Placement into the Coronary Sinus under Direct Vision Using a Balloon-Tipped Cardioscope" PACE, Sep. 1998; 21: 1724-1729.

* cited by examiner

METHOD FOR VISUALIZING TISSUE WITH AN ICG DYE COMPOSITION DURING ABLATION PROCEDURES

CROSS-REFERENCE TO RELATED APPLICATIONS

This application is a divisional of U.S. Non-Provisional patent application Ser. No. 14/697,065, filed on Apr. 27, 2015, which is based on and claims priority to U.S. Provisional Patent Application Ser. No. 61/985,142, filed on Apr. 28, 2014, all of which are incorporated by reference, as if expressly set forth in their respective entireties herein.

TECHNICAL FIELD

The present disclosure relates to ablation instruments and methods of use thereof, in particular to ablation catheters and methods for visualizing tissue using an ICG dye composition to identify and distinguish ablative tissue from de novo tissue.

BACKGROUND

Cardiac arrhythmias (e.g., fibrillation) are irregularities in the normal beating pattern of the heart and can manifest themselves in either the atria or the ventricles of the heart. For example, atrial fibrillation is a form of arrhythmia characterized by rapid randomized contractions of atrial myocardium, causing an irregular, often rapid ventricular rate. The regular pumping function of the atria is replaced by a disorganized, ineffective quivering as a result of chaotic conduction of electrical signals through the upper chambers of the heart. Atrial fibrillation is often associated with other forms of cardiovascular disease, including congestive heart failure, rheumatic heart disease, coronary artery disease, left ventricular hypertrophy, cardiomyopathy, or hypertension.

It is now understood that recurrent atrial fibrillation (paroxysmal and persistent) is triggered by rapidly firing tissue, (called "ectopic foci"), that are located in one or more of the four pulmonary veins, which attach to the rear of the left atrium. It has been found that atrial fibrillation may be cured by electrically isolating the pulmonary veins from the rest of the atrium.

Various techniques have been employed for pulmonary vein isolation. A common purpose of each of these techniques is to replace cardiac muscle cells with scar tissue, which scar tissue cannot conduct normal electrical activity within the heart.

In one known approach, circumferential ablation of tissue at the junction of the pulmonary veins and the left atrium has been practiced to treat atrial fibrillation. By ablating the heart tissue at selected locations, electrical conductivity from one segment to another can be blocked and the resulting segments become too small to sustain the fibrillatory process on their own.

Several types of ablation devices have recently been proposed for creating lesions to treat cardiac arrhythmias. Many of the recently proposed ablation instruments are percutaneous devices that are designed to create such lesions from within the heart. Such devices are positioned in the heart by catheterization of the patient, e.g., by passing the ablation instrument into the heart via a blood vessel, such as the femoral vein.

Typically, percutaneous devices are positioned with the assistance of a guide catheter and guide wire, which are first advanced into heart. In one common approach, a guide catheter or similar guide device is advanced through the vasculature and into the left atrium of the heart. A guide wire is then advanced toward a pulmonary vein. A catheter instrument with an expandable element is then advanced through the guide catheter and over the guide wire and into the pulmonary vein where the expandable element (e.g., a balloon) is inflated. The balloon includes a circumferential ablation element, e.g., an energy emitting device, such as a laser, disposed in the inner surface of the balloon, which performs the ablation procedure.

It is noted that ablation near or within the pulmonary vein can result in complications. Overtreatment deep within a vein can result in stenosis (closure of the vein itself), necrosis or other structural damage, any of which can necessitate immediate open chest surgery. Conversely, undertreatment in which scar tissue formed is not continuous and/or insufficient to replace the cardiac muscles sought to be electrically isolated from the atrium will cause the surgical ablation procedure to be unsuccessful. Thus, repeating of the surgical ablation procedure is then required which is almost always undesirable.

Currently, when laser energy has been applied to a region of tissue at an ostium of the PV there is little to no visible change to that region of tissue when viewed through an endoscope thereby presenting the problem of distinguishing treated tissue (e.g., lesion) from de novo tissue.

The lesions are not visible for various reasons. For example, the ablation energy in these procedures typically penetrates deeply into the atrial tissue to create the lesion while leaving the endocardial surface relatively undamaged. Additionally, color video cameras are often not sensitive enough to discriminate the subtle color changes that distinguish treated and untreated tissue. Also, the light levels delivered to the site are limited since they typically travel to the treatment site via a small optical fiber thereby further hindering the ability of video cameras to visualize these distinctions.

Thus, there remains a need in the art for systems and methods configured to accurately and immediately discriminate lesions from de novo tissue, thereby allowing the user (surgeon or more specifically and electrophysiologist or interventional radiologist) to take corrective action in real time to ensure a complete lesion is formed.

SUMMARY

The present invention is directed to the use of an indocyanine green (ICG dye) composition as part of an imaging system for distinguishing lesions from de novo tissue. A tissue ablation system for identification of a lesion formed by directed energy emission at a surgical site of a patient includes a source of an indocyanine green (ICG dye) composition for delivery into a body of the patient including to the surgical site. The system further includes a tissue ablation instrument for use at the surgical site. The instrument includes a movable directed first energy emitter configured to emit a variable amount of directed energy for ablating tissue and forming a lesion at the surgical site. A second energy emitter is provided for applying energy of a type and in an amount sufficient to cause the ICG composition to fluoresce. The system further includes an imaging device that is configured to obtain an image of the surgical site while the ICG fluoresces with the lesion being visually identifiable relative to de-novo tissue based on a lack of observable fluorescence at locations of the lesion, while the de-novo tissue is characterized by areas of fluorescence. A display, such as a computer monitor, displays the image in real time.

Since the formed lesion is immediately and readily visually distinguishable from the de novo tissue and blood due to the bright fluorescence of the de novo tissue and blood versus the formed lesion being characterized by a lack of fluorescence, the user (surgeon) can detect deficiencies in the lesion, such as gaps or breaks in the lesion, and take immediate corrective measures.

These and other aspects, features and benefits of the invention can be further appreciated from the accompanying drawings, which illustrate certain embodiments of the invention together with the detailed description thereof.

BRIEF DESCRIPTION OF THE DRAWINGS

The objects and features of the invention may be understood with reference to the following detailed description of an illustrative embodiment of the present invention taken together in conjunction with the accompanying drawings in which.

DETAILED DESCRIPTION OF CERTAIN EMBODIMENTS OF THE INVENTION

The present invention will now be described more fully with reference to the accompanying drawings, in which illustrated embodiments of the present invention are shown. The present invention is not limited in any way to any of the illustrated embodiments.

In accordance with the present invention and as described in detail below, a visualization system/method that uses ICG dye for distinguishing ablated tissue from de novo tissue.

Indocyanine green (ICG) is a cyanine dye used in medical diagnostics. ICG dye has the following formula:

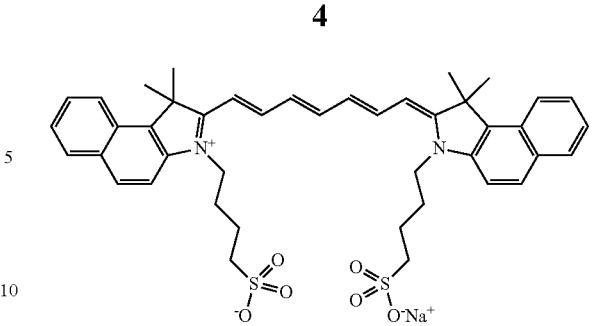

ICG dye is traditionally used for determining cardiac output, hepatic function, and liver blood flow, and for ophthalmic angiography. It has a peak spectral absorption at about 800 nm. These infrared frequencies penetrate retinal layers and other tissue allowing ICG angiography to image deeper patterns of circulation than fluorescein angiography. ICG binds tightly to plasma proteins and becomes confined to the vascular system. ICG has a half-life of 150 to 180 seconds and is removed from circulation exclusively by the liver to bile juice.

ICG is a fluorescent dye which is used in medicine as an indicator substance (e.g. for photometric hepatic function diagnostics and fluorescence angiography) in cardiac, circulatory, hepatic and ophthalmic conditions. ICG is typically administered intravenously and, depending on liver performance, is eliminated from the body with a half-life of approximately 3-4 minutes. ICG sodium salt is normally available in powder form and can be dissolved in various solvents; 5% (<5% depending on batch) sodium iodide is usually added to ensure better solubility. The sterile lyophilisate of a water-ICG solution is approved in many European countries and the United States under the names ICG-Pulsion and IC-Green as a diagnostic for intravenous use.

The absorption and fluorescence spectrum of ICG is in the near infrared region. Both depend to some degree on the solvent used and the concentration. ICG absorbs mainly between 600 nm and 900 nm and emits fluorescence between 750 nm and 950 nm. The large overlapping of the absorption and fluorescence spectra leads to a marked reabsorption of the fluorescence by ICG itself. The fluorescence spectrum is very wide. Its maximum values are approximately 810 nm in water and approximately 830 nm in blood. For medical applications based on absorption, the maximum absorption at approximately 800 nm (in blood plasma at low concentrations) is important. In combination with fluorescence detection, lasers with a wavelength of around 780 to 815 nm are used. At this wavelength, ICG still absorbs very well and yet it is still technically possible to suppress the excitation light in order to detect the fluorescence.

Figure 1:
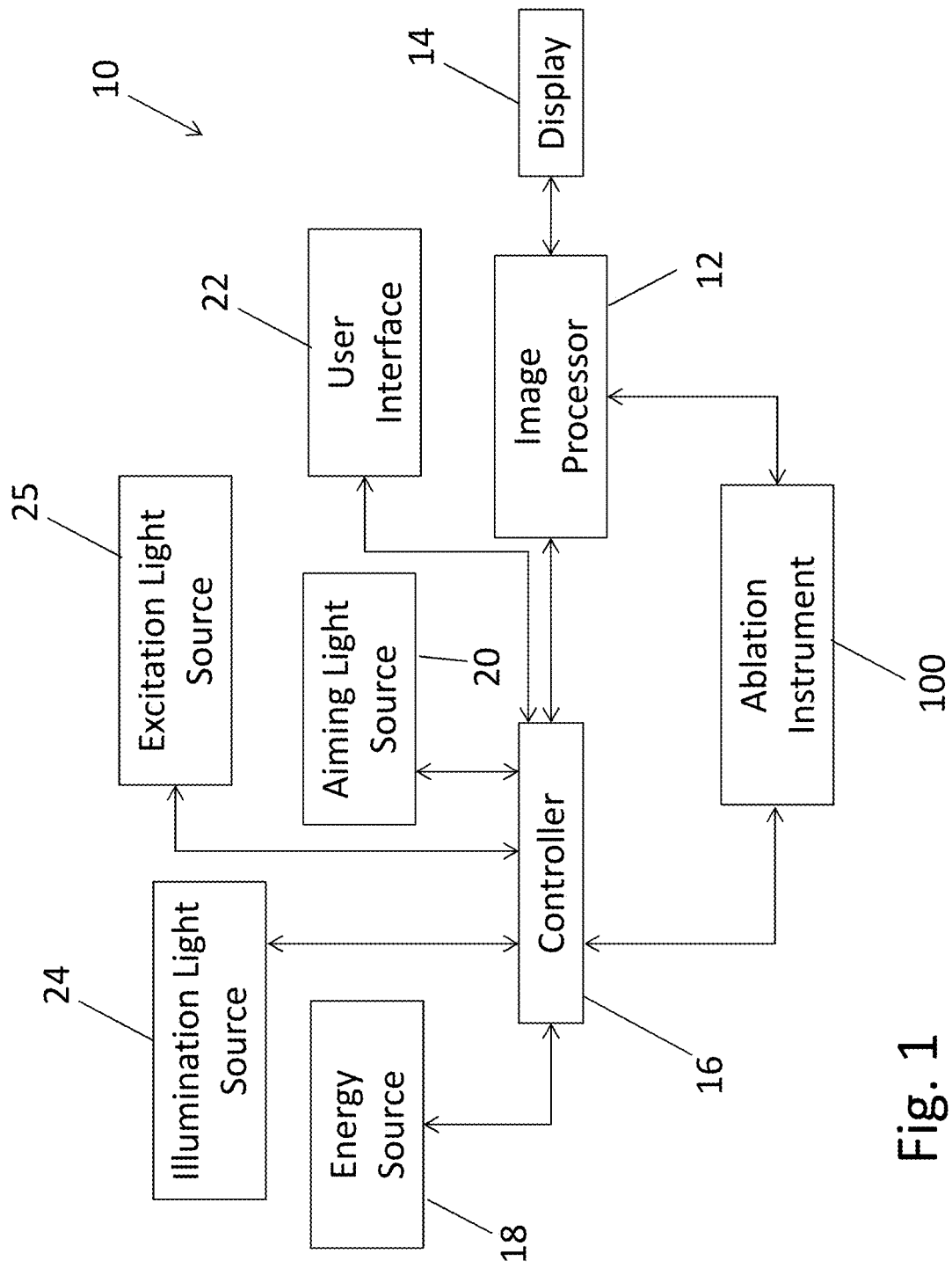
FIG. 1 is a block diagram depicting the components of an endoscope-guided cardiac ablation system according to the invention.

FIG. 1 is a schematic block diagram illustrating an ablator/endoscopic system in accordance with the invention, designated generally by reference numeral 10. Ablator system 10 preferably includes a surgical ablation instrument 100 preferably including an endoscope and ablation instrument as discussed below. The surgical ablation instrument 100 can be any number of different ablation instruments that are commercially available including those disclosed by Applicant in previous U.S. patents and patent applications (e.g., U.S. patent application publication Nos. 2009/0326320 and 2011/0082451, each of which is hereby incorporated by reference in its entirety). In general, the ablation instrument 100 is of a type that emits ablation energy sufficient to cause formation of an ablation at a tissue target site.

The ablator system 10 further preferably includes an aiming light source 20 and an illumination light source 24. A processor 12 designed to accept input and output data from the connected instruments, display and controller and process that data into visual information. Also included is an excitation light source YY that emits light in the wavelength range adequate to excite the ICG dye fluorescence. In some embodiments the illumination light source 24 may be identical to the excitation source YY. Alternatively the illumination light source 24 may provide a broadband white light illumination for normal endoscopic imaging and then be converted to an excitation light source by using an optical filter to remove wavelengths away from the absorption peak of ICG.

As will also be appreciated from the below discussion, an endoscope is preferably provided in ablation instrument 100 and has the capability of capturing both live images and recording still images. An illumination light is used to provide operating light to the surgical site. The illumination light is of a frequency that allows the user to differentiate between different tissues present at the operating site. An aiming light source 20 is used to visualize the location where energy will be delivered by the ablation instrument 100 to tissue. It is envisioned that the aiming light will be of a wavelength that can be recorded by an image capture device and visible on a display.

Composite Imaging System

The processor 12 is designed to process live visual data as well as data from the ablation instrument controllers and display. The processor is configured execute a series of software and/or hardware modules configured to interpret, manipulate and record visual information received from the surgical site. The processor 12 is further configured to manipulate and provide illustrative and graphical overlays and composite or hybrid visual data to the display device.

As seen in FIG. 1, the system 10 further includes a controller 16, an energy source 18, aiming light source 20 and a user interface 22. Controller 16 is preferably configured to control the output of the energy source 18 and the illumination and excitation sources 24 and 25 of an energy transmitter as well as determine the distance and movement of an energy transmitter relative to tissue at an ablation surgical site (as discussed further below). As will also be appreciated from the below discussion, an endoscope is preferably supported by the ablation instrument 100 and captures images that can be processed by the processor 12 to determine whether sufficient ablative energy deliveries have been directed to a specific area of a surgical site. Data obtained from the endoscope includes real-time video or still images of the surgical site as seen from the ablation instrument.

The aiming light source 20 is used to visualize the surgical site location 120 where energy will be delivered by the ablation instrument 100 to tissue 130. Preferably, the aiming light source 20 outputs light in a visible region of the electromagnetic spectrum. If a suitable ablation path is seen by the user, the controller 16 transmits radiant energy, via energy source 18, from the ablation instrument 100 to a target tissue site 120 to effect ablation by lesions. It is to be appreciated that the term "radiant energy" as used herein is intended to encompass energy sources that do not rely primarily on conductive or convective heat transfer. Such sources include, but are not limited to, acoustic, laser and electromagnetic radiation sources and, more specifically, include microwave, x-ray, gamma-ray, ultrasonic and radiant light sources. Additionally, the term "light" as used herein is intended to encompass electromagnetic radiation including, but not limited to, visible light, infrared and ultraviolet radiation.

The illumination light source 24 is a light source used to provide proper illumination to the surgical site. The illuminate is configured so that natural biological tones and hues can be easily identifiable by an operator.

The controller 16 can provide the user with the ability to control the function of the aiming light source, the user input devices, and the ablation instrument. The controller serves as the primary control interface for the ablation system. Through the controller, the user can turn on and off both the aiming and illumination lights. Furthermore the controller possesses the ability to change the illumination and aiming light intensity. The ability to switch user interfaces or display devices is also envisioned. Additionally, the controller gives access to the ablation instrument, including control over the intensity of the discharge, duration and location of ablative energy discharges. The controller 16 can further provide a safety shutoff to the system in the event that a clear transmission pathway between the radiant energy source and the target tissue is lost during energy delivery (e.g., see commonly owned U.S. patent application Ser. No. 12/896,010, filed Oct. 1, 2010, which is hereby incorporated by reference in its entirety.

The controller can be separate microprocessor based control interface hardware or it can be a portion of a configured as a module operating through a processor based computer system configured to accept and control inputs from various physical devices.

Figure 3:
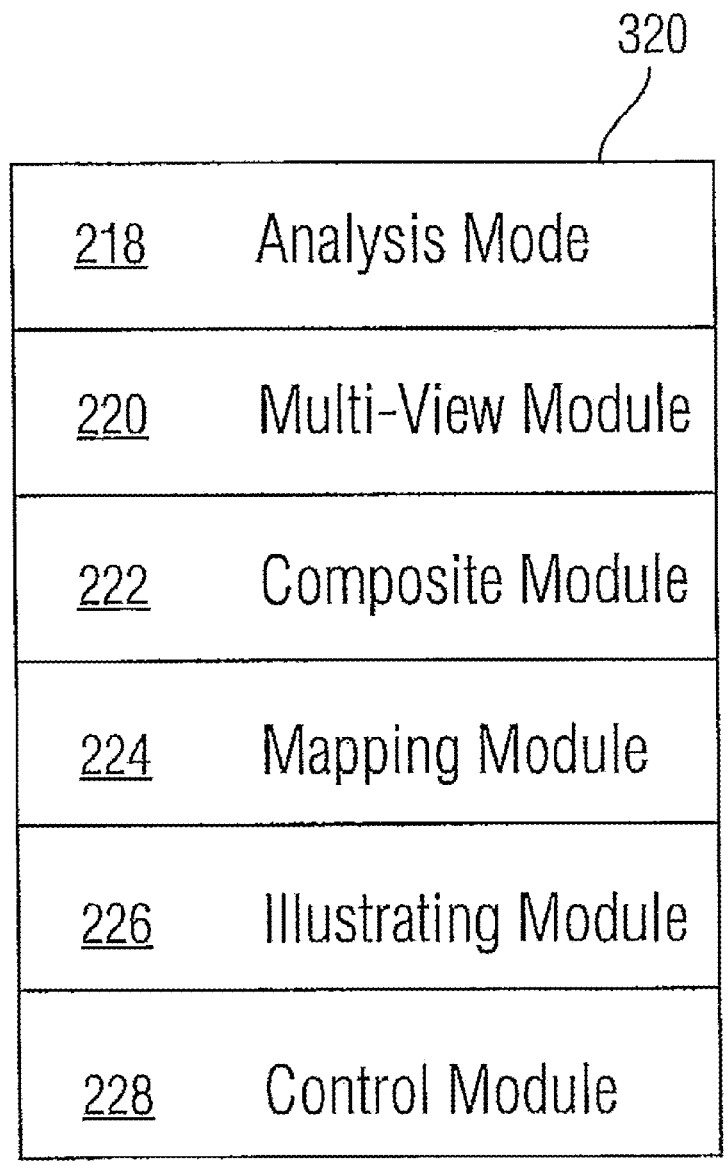
FIG. 3 is a block diagram of the processor modules used in the cardiac ablation instrument.

As shown in FIG. 3, a set of modules cooperate with one another to provide the information presented through the interface of the system of FIG. 1. Thus, for example, there is an analysis module 218, a multiple view module 220, a composite module 222, a mapping module 224, an illustrating module 226, and a control interface module 228. Each of these modules can comprise hardware, code executing in a processor, or both, that configures a machines such as a workstation to implement the functionality described herein.

With further reference to FIG. 3, the analysis module 218 includes instructions for analyzing a lesion and determining if it is sufficient for the desired treatment. The analysis module is configured to inspect the image data captured by the image capture device and a lesion of sufficient dimensions and quality has been formed. The analysis module 218 can be implemented as discrete sub-modules to provide functions such as receiving data on the duration and intensity of an ablative emission. An additional sub module is capable of evaluating the duration of the energy emission and comparing it to a look up table of sufficient duration and intensity values suitable to form a proper lesion.

The multiple view module 220 includes instructions for configuring the processor 12 to provide multiple images to the display. The multiple view module configures the display to depict at least two image depiction areas. In a first image depiction area, the live video stream of the surgical site is displayed to the user. In a second image depiction area, a still image, highlighting the last target of ablative energy is depicted.

The composite module 222 includes instructions for combining a series of still images and producing a composite image that depicts the target location of the ablative emission in each still image. The compositing module 222 can be implemented as discrete sub-modules to provide functions such as altering the transparency of each still image layer of the composite image so that a time based map of ablation locations can be produced. Another function implemented by the submodules is construction of a video or slideshow from a sequence of still images.

The mapping module 224 includes instructions for overlaying proposed treatment paths on the live image. The mapping module is configured to show showing colored markers indicating acceptable levels of ablative energy depositing. For example the mapping module is capable of generating a green colored visual marker and superposing it over the live image to indicate areas that have yet to receive levels of ablative energy necessary for treatment. Conversely, the mapping module 224 is also capable of simultaneously generating a red colored (or other color) visual marker and superimposing it over the live image to indicate areas that have received sufficient quantities of ablative energy suitable lesions. The mapping module 224 can be implemented as discrete sub-modules to provide functions such as receiving data on the duration and intensity of an ablative emission and correlating that specific instance to a specific stored image.

Figure 8:
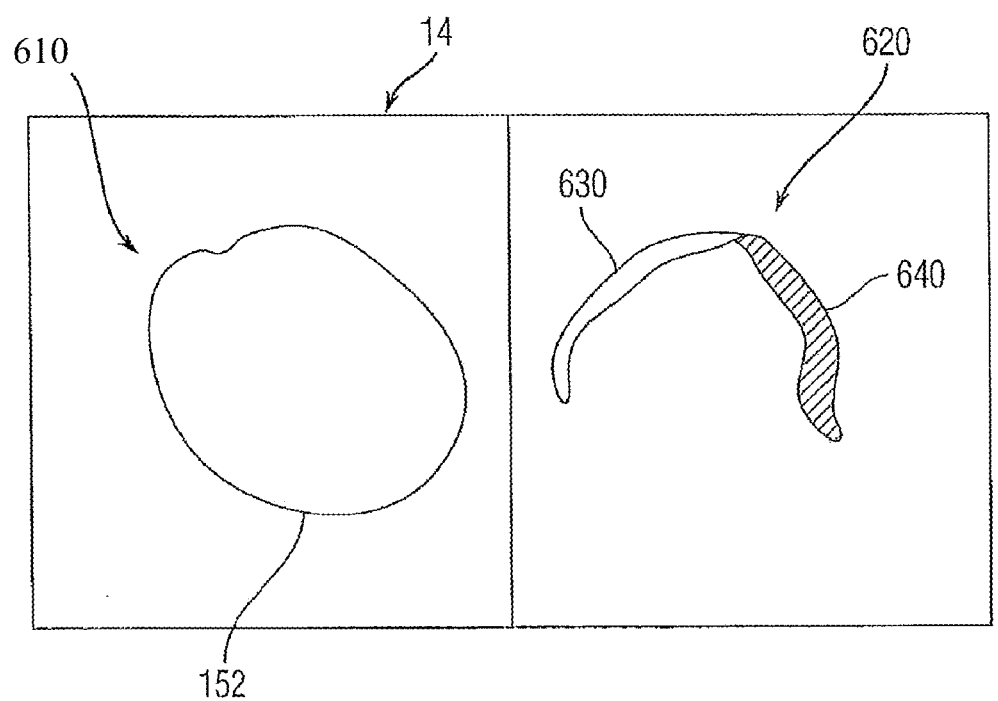
FIG. 8 is a screen shot of the display of FIG. 1 depicting visual warning signals indicative of insufficient lesions.

The illustrating module 226 includes instructions for providing an image to the display, wherein the image is an illustration or graphical representation of the surgical site. The illustrating module 226 is configured to allow annotation of the illustrated image as well as comparison between the live image and the illustrated image. For example, and as shown in FIG. 8, display 14 provides a first screen portion 610 depicting the actual surgical site 152 as viewed from endoscope 176. Display 14 also illustrates a second screen portion 620 illustrating a graphical depiction of the surgical site 152 indicating the actual path of the energy transmitter 140 on the tissue at the surgical site wherein the path consists of a trace indicating the sufficiency of the formed lesions in which a solid trace 630 indicates sufficient lesions and a hashed trace 640 indicates insufficient lesions.

The control module 220 includes instruction for orientating and accessing the functions of each of the other modules, as well as communicating with the controller and inputting information or manipulating the parameters of the data being displayed during operation. The manipulation and controlling functions can be implemented as discrete sub-modules with instructions for selecting operation modes, control interfaces, display orientation, recording modes, storage device location and data entry.

Figure 4:
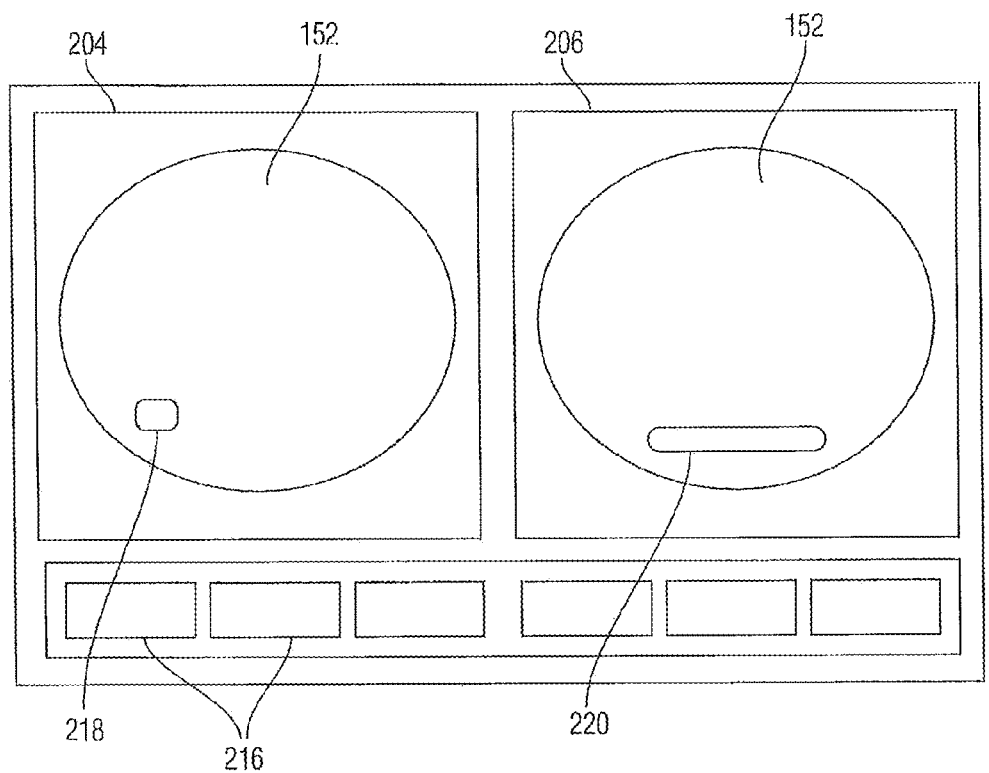
FIG. 4 illustrates a user interface in the form of a splint-screen arrangement for displaying information.

The user refers to the live video feed from the image capture device to determine where to direct a radiant energy transmission. Upon first use of the device, a live video image and a still image of the surgical site are depicted on the display. As seen in FIG. 4, the processor 12 outputs to the display 14 at least two separately defined image depiction areas 204, 206. One image depiction area 204 is reserved for displaying live video transmitted from the surgical site 152. At least one other image depiction area 206 is used to depict an image or a composite image comprised of several still images representing specific moments in time during the surgical procedure.

The live video shown to the user will allow the user to see the reflection of the aiming light 218 and hence direct ablative energy. It is envisioned that the first still image 210 depicted will be a still image captured at a point in time prior to the initiation of the first radiant energy emission. For instance, at a point in time prior to the emission of radiant energy, the image capture device records an image 210 of the surgical site 152 that depicts the surgical site 152 without the aiming light. By taking a still image 210 of the site, the user can record a baseline image of the surgical site before any treatment has been commenced. Furthermore, through the functions of the illustrative module, an illustration of the untouched 152 can be generated. During emission of radiant energy a still image 210 is taken of the surgical site 152. The characteristics of the ablative event (e.g. information regarding the duration and intensity of the radiant of the energy emission) are stored and associated with the image depicting that specific emission. In addition, the reflection the aiming light will be visible in the still image, providing a location indicator as to where the energy was directed. A series of these still images can be combined by using the composite module. By modifying the opacity of each image, the reflected light of the aiming light for each ablative event will be visible in the composite image. In this way, a complete record 220 of where energy was directed will becomes available. Furthermore, because the composite image is composed a series of individual images representing a specific period of time during the procedure, a time based map of the entire operation can also be produced in real time or for subsequent review.

Also visible in FIG. 4 are control interfaces 216 for accessing the control module. The control interfaces allow the user to select image style and opacity as well and initiating the functions of the other modules. Furthermore the functions of the controller 16 are also controllable from the control interface.

It is to be appreciated the invention is not to be understood to be limited to the two image depiction areas discussed above with reference to FIG. 3 or 4, but rather may encompass any number of image depiction areas in which the images and representations of the surgical site 152 can be reviewed. With reference to FIG. 8 the images shown by the display 14 can be manipulated by the modules to illustrate the presence of sufficient or insufficient lesion formation. For instance, the display 14 may illustrate the image of the surgical site 152 viewed from the endoscope 176 wherein varying shades of grey and white depict tissue and lesions and in the event insufficient lesions are determined to be formed, or a red marker can be superimposed on the image of the surgical site 152 at the location where the insufficient lesion was determined. Coincidently, an audio signal may also be emitted from ablator system 10 causing further warning to the user.

Therefore, if the user is not satisfied with the quality of the lesion produced, or the modules indicate that a sufficient lesion was not produced, the user can promptly redo the treatment of a specific tissue location (spot treatment). Conversely, if the modules indicate that a sufficient lesion was formed, the user can confidently move on to a new tissue location to continue the treatment thus saving time and effort by avoiding the need to more closely examine the tissue location that was just treated. Hence, once the entire treatment is performed, the modules of the system permit the surgeon to view all treatment segments forming the entire ablation arc to see if a continuous, uninterrupted ablation has been formed (or see if the ablation has the intended, desired shape). If there are visible gaps or other imperfections with the formed ablation, the surgeon can move the energy transmitter 140 to the proper location for retreatment of these areas until the desired ablation is formed. The process can then be repeated to determine and confirm that the gap was eliminated.

As a result, the mapping, analyzing and illustrating functions performed by the ablation system of the present invention overcome the disadvantages associated with prior ablation surgical procedures and results in increased ablation success rates due to a more optimal and more accurate viewing and quality determination of the spot lesions created to form the continuous ablation at the tissue location for the surgical site 152.

Figures 5, 6:
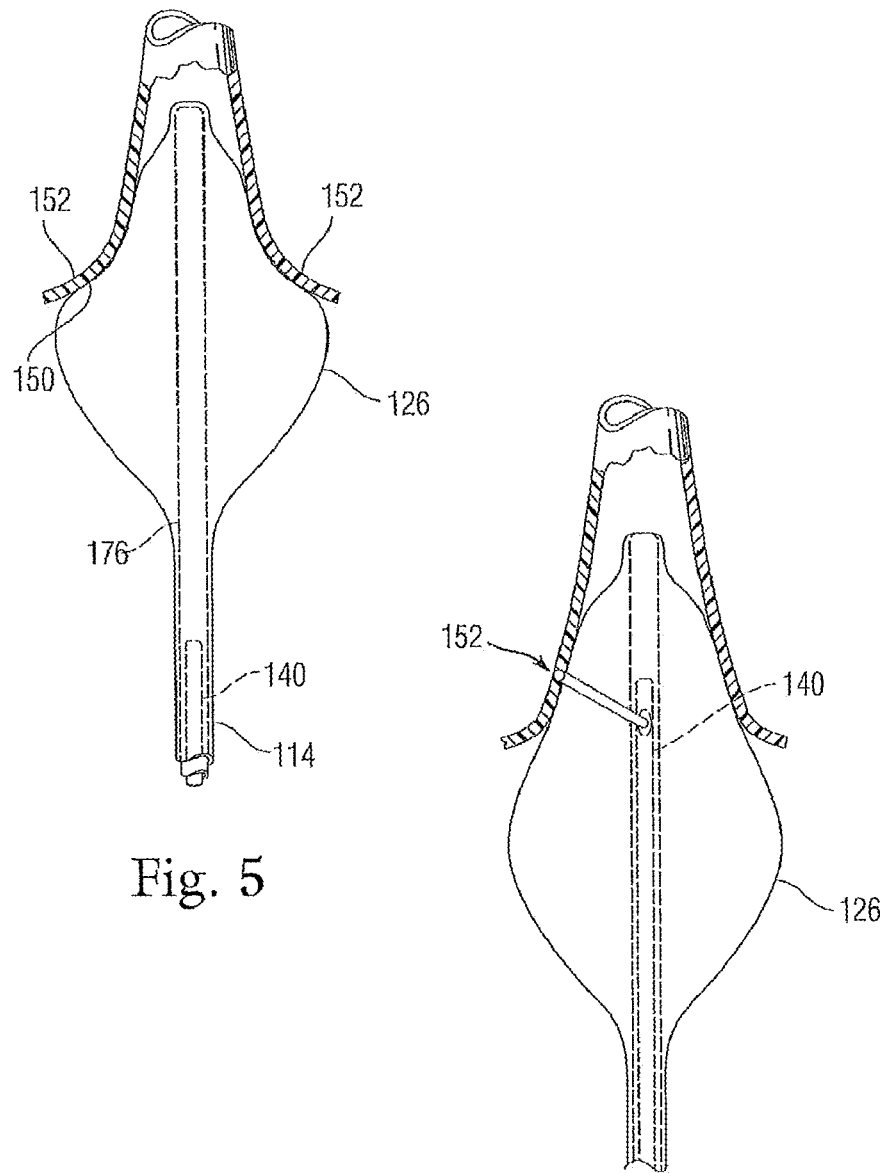
FIG. 5 is a schematic view of the cardiac ablation instrument of FIG. 2 shown in a treatment position at a surgical site in the pulmonary vein.
FIG. 6 is a schematic view of the cardiac ablation instrument of FIG. 2 with its compliant balloon inflated and its ablation element deployed at one of a plurality of locations.

With reference now to FIG. 5, a description of ablation instrument 100 is provided. FIG. 5 provides a schematic, cross-sectional view of an ablation instrument 100, including an elongate body 114, a central lumen tubing 116 and a compliant balloon 126 inflatable via one or more ports 122 in the central tubing 116. The central tubing 116 can also house an energy emitter that is capable of both axial movement and rotation within a lumen formed in the elongate body 114. The energy emitter is also described herein as being an energy transmitter, an energy emitter (or lesion generator), a radiant energy emitter and a radiant energy transmitter (ablation element). Additionally formed in the elongated body 114 (also referred to herein as the catheter body) there can be a plurality of additional lumens, through which certain devices or instruments can be passed. For example, the catheter body 114 also provides lumens 118A and 118B for extraction (or circulation) of an inflation fluid, an endoscope 176 and illumination and excitation fibers 128A and 128B.

It should be understood that the embodiments illustrated in the drawings are only a few of the cardiac ablation instruments that can be utilized in accordance with the present invention. Further descriptions of other embodiments can be found, for example, in commonly owned, co-pending U.S. patent application Ser. No. 10/357,156, filed Feb. 3, 2003, U.S. patent application Ser. No. 09/924,393, filed Aug. 7, 2001, each of which is expressly incorporated by reference.

With reference now to FIGS. 5-6, the ablation instrument 100 is preferably designed such that upon disposition within the heart (e.g., proximal to a pulmonary vein), the balloon 126 can be inflated such that a shoulder portion 150 of the balloon 126 will be urged into close proximity with a target region 152 of cardiac tissue. As shown in FIG. 4, the energy emitter (or "lesion generator") 140 can be positioned to delivery ablative energy to the target region 152 to form a continuous lesion. The term "continuous" in the context of a lesion is intended to mean a lesion that substantially blocks electrical conduction between tissue segments on opposite sides of the lesion.

Figure 2:
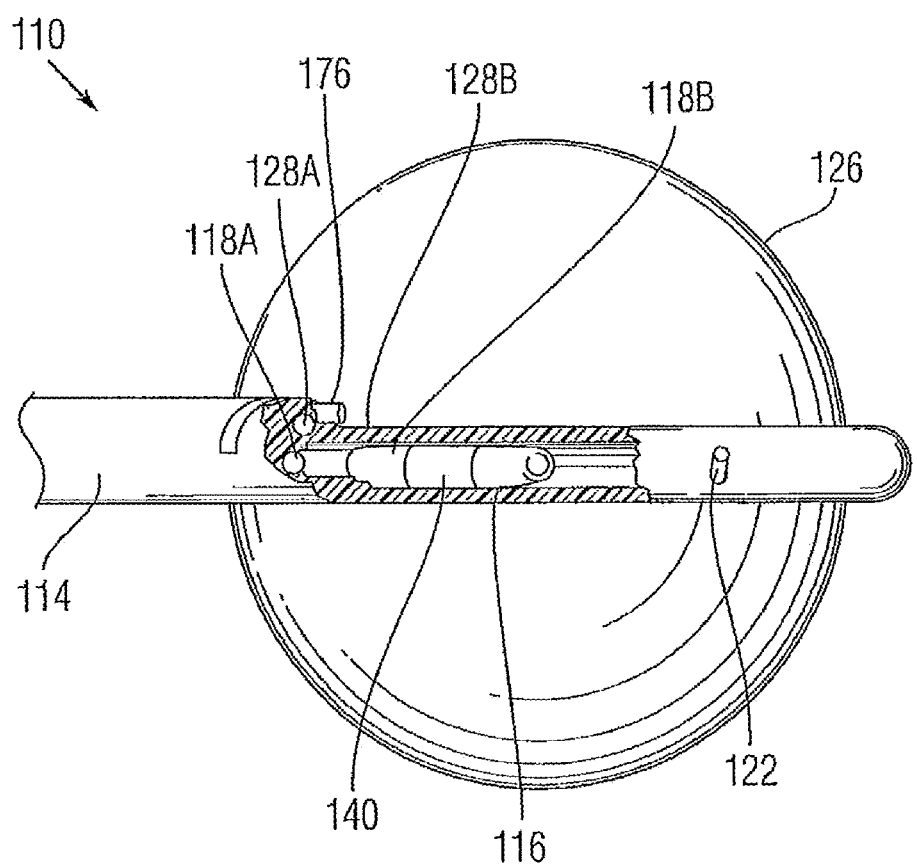
FIG. 2 is a schematic view of the of the cardiac ablation instrument of the cardiac ablation system of FIG. 1.

The radiant energy emitter 140 is shown in FIG. 2 disposed within the balloon 126 remotely from the target tissue (e.g., within a central lumen 116 of the catheter body 114 or otherwise disposed within the balloon). In one illustrated embodiment, the radiant energy transmitter (ablation element) 140 includes at least one optical fiber coupled to a distal light projecting, optical element, which cooperate to project a spot of ablative light energy through the instrument 100 to the target site 152 (in FIG. 6). The catheter body 114, projection balloon 126 and inflation/ablation fluids are all preferably substantially transparent to the radiant energy at the selected wavelength of the energy source as well as to the absorption and emission wavelengths of ICG dye to provide a low-loss transmission pathway from the radiant energy transmitter 140 to the target site 152. It should be understood that the term "balloon" encompasses deformable hollow shapes which can be inflated into various configurations including spherical, obloid, tear drop, etc., shapes dependent upon the requirements of the body cavity. Such balloon elements can be elastic or simply capable of unfolding or unwrapping into an expanded state. The balloon can further encompass multiple chamber configurations.

Also disposed within the instrument 100 is a reflectance sensor, preferably an endoscope 176 capable of capturing an image of the target site 152 and/or the instrument position. The endoscope 176 is typically an optical fiber bundle with a lens or other optical coupler at its distal end to receive light. The reflectance sensor/endoscope can also include an illumination source, such one or more optical fibers coupled to a light source or sources. Alternatively illumination and excitation light may be delivered though separate optical fibers as indicated by 128A in FIG. 2. Endoscopes are available commercially from various sources. The endoscope can further include an optical head assembly, as detailed in more detail below, to increase the field of view. In one illustrated embodiment, ablation element 140 and endoscope 176 are adapted for independent axial movement within the catheter body 14.

The term "endoscope" as used herein is intended to encompass optical imaging devices, generally, including but not limited to endoscopes, fiberscopes, cardioscopes, angioscopes and other optical fiber-based imaging devices. More generally, "endoscope" encompasses any light-guiding (or waveguide) structure capable of transmitting an "image" of an object to a location for viewing, such as display 14.

Preferably, spot lesions are formed at the target site 152 by applying radiant energy from the energy transmitter 140 to target tissue. The applied radiant energy may be applied in an energy range from about 50 Joules/cm$^2$ to about 1000 Joules/cm$^2$, or preferably from about 75 Joules/cm$^2$ to about 750 Joules/cm$^2$. The power levels applied by the energy emitter can range from about 10 Watts/cm$^2$ to about 150 Watts/cm$^2$ and the duration of energy delivery can range from about 1 second to about 1 minute, preferably from about 5 seconds to about 45 seconds, or more preferably from about 10 to about 30 seconds. For example, for power levels between 10 and 75 Watts/cm$^2$ it can be advantageous to apply the radiant energy for about 30 seconds. Lesser durations, e.g., of 10 to 20 seconds, can be used for power levels of 75 to 150 Watts/cm$^2$. It is to be understood the above figures are provided as examples and the energy, power and time duration figures set forth above are provided merely as examples and are not to be understood to be limited thereto.

In the illustrated embodiment of the ablation instrument 100 shown in FIGS. 5-6, the energy emitter 140 is a radiant energy emitter including at least one optical fiber coupled to a distal light projecting optical element, which cooperate to project a spot of ablative light energy through the instrument 100 to the target site 152. The optical element can further comprise one or more lens elements and/or refractive elements capable of projecting a spot or arc-shaped beam of radiation. Alternatively, the lesion generator may generate an annulus or partial ring of ablative radiation, as described in more detail in commonly owned U.S. Pat. No. 6,423,055 issued Jul. 22, 2002, herein incorporated by reference for its disclosure related thereto.

Since the radiant energy (e.g., a laser) emitted from the energy emitter 140 is typically outside the visual light spectrum that can be detected by the human eye, the ablation instrument 100 includes an aiming light preferably having a pulsed operating mode in which visible light from the aiming light unit is delivered in pulses to cause intermittent illumination of the tissue at the target site 152. This gives the aiming light an appearance of being a blinking light. By delivering the visible aiming light in pulses, the surgeon is able to directly observe the tissue that is being treated at the target site 152, using an endoscope, between the aiming light pulses.

During a surgical ablation procedure, the endoscope 176 is used to determine the extent of tissue ablation by sensing the change in color of the tissue as it is ablated and at a time when the aiming beam is in an off cycle via the display 14. In other words, between the blinking (pulses) of the aiming light, the surgeon can observe the treated tissue to determine how the treatment is progressing since the endoscope 176 is used to determine the extent of tissue ablation by sensing the change in color of the tissue as it is ablated and at a time when the aiming beam is in an off cycle. However, many conditions may cause the actual detection of change in color of tissue being ablated to be difficult and/or unreliable in regards to whether proper spot lesions are formed by the energy transmitter 140 on the tissue at the ablation surgical site 152. For instance, insufficient illumination at the surgical site 152 can make it difficult, if not impossible, to ascertain whether proper spot lesions were formed at the surgical site as viewed on display 14.

Figure 7:
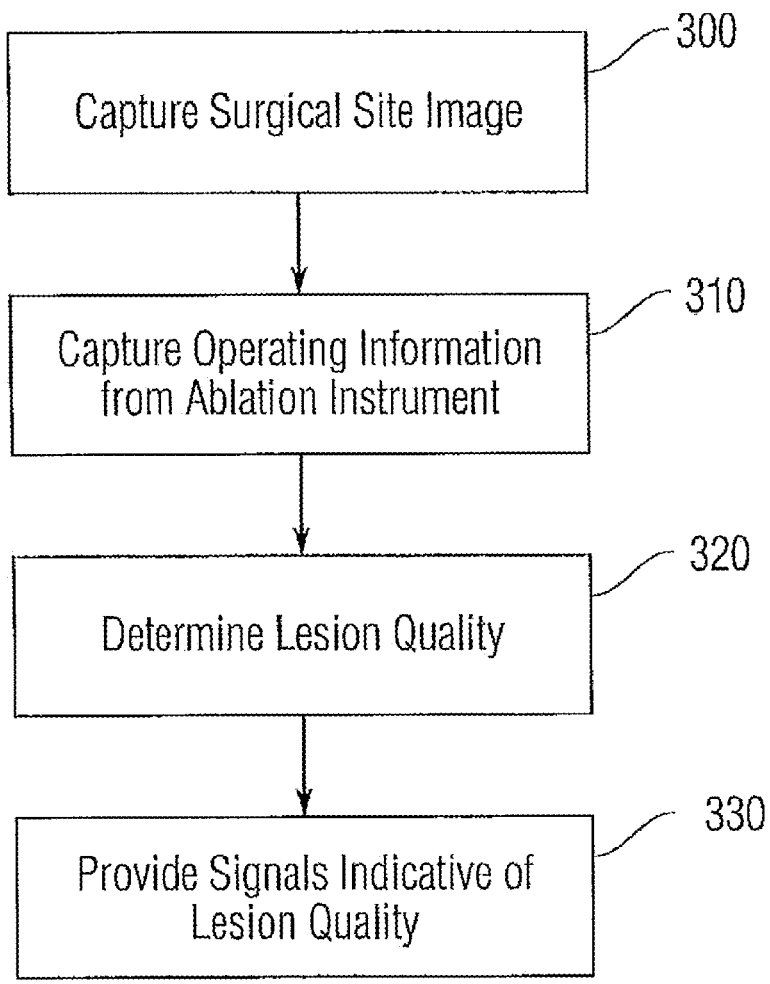
FIG. 7 is a flow diagram illustrating the steps performed by the ablator system of FIG. 1 for determining the quality of lesions formed during a surgical ablation procedure.

The processor 12 of ablator system 10 obviates this problem by determining the quality of the lesion formed on the tissue at the target site 152 which may be viewed on monitor 14 and/or indicated to a surgeon visual overlay or audio cues. With reference now to the flow diagram of FIG. 7, the method of operation for determining the quality of spot lesions at an ablation surgical site 152 will now be discussed.

Starting at step 300, the processor 12 captures the image from endoscope 176 of the tissue being ablated at the surgical site. At step 310, the processor 12 also captures information relating to the energy transmitter 140 from controller 16. The captured energy transmitter 140 information includes: the amount of radiant energy (power) applied by energy transmitter 140 on the tissue at the surgical site 152 to form spot lesions; the distance the energy transmitter 140 is from tissue to be ablated via spot lesions; and the rate of movement of energy transmitter 140 relative to the tissue at the surgical site 152. It is to be appreciated that aforesaid information captured regarding energy transmitter 140 is not to be understood to be limited thereto as more or less information may be captured that is necessary to determine the quality of the spot lesions formed on the tissue at the surgical site.

The processor 12 then preferably uses algorithmic techniques to determine whether a sufficient spot lesion has just recently been formed on the tissue at the surgical site (step 320). In other words, given the distance the energy transmitter 140 is located from the tissue at the surgical site 152, the rate of movement of the energy transmitter 140 relative to the tissue at the surgical site 152 (e.g., the amount of time that energy is applied to the tissue at a given location), and the amount of energy being applied, a determination is made as to whether a sufficient spot lesion has been formed on the tissue at a location which the energy transmitter is applying ablation energy thereto. A lookup table or other similar means may also be used by processor 12 for determining the aforesaid lesion quality. A spot lesion is to be understood as being sufficient when it comprises enough scar tissue effective to block the transmission of electrical signals therethrough.

The processor 12 is preferably further operative and configured to provide a signal to the surgeon indicative of whether a sufficient spot lesion has been formed (step 330). This indicative signal may be provided in the event an insufficient or no spot lesion was formed on the tissue at the surgical site 152 that was subject to the energy transmitter 140 dispersing energy thereto. This indicative signal may be an audio and/or visual signal. The audio signal may consist of a warning tone and the visual signal may consist of a marker (e.g., color red) superimposed on the display 14 illustrating the surgical site 152 (provided via endoscope 176) at the location at which the insufficient spot lesion was determined. Thus, when image processor 12 determines an insufficient spot lesion has been formed, the aforesaid warning signal is promptly provided to the surgeon enabling the surgeon to revisit the tissue having the insufficient lesion and make proper adjustments with the energy transmitter 140 (e.g., apply more energy, close the distance between energy transmitter 140 and the surgical site and/or slow the movement of energy transmitter 140 relative to the surgical site) so as to now form sufficient lesions.

Figure 9:
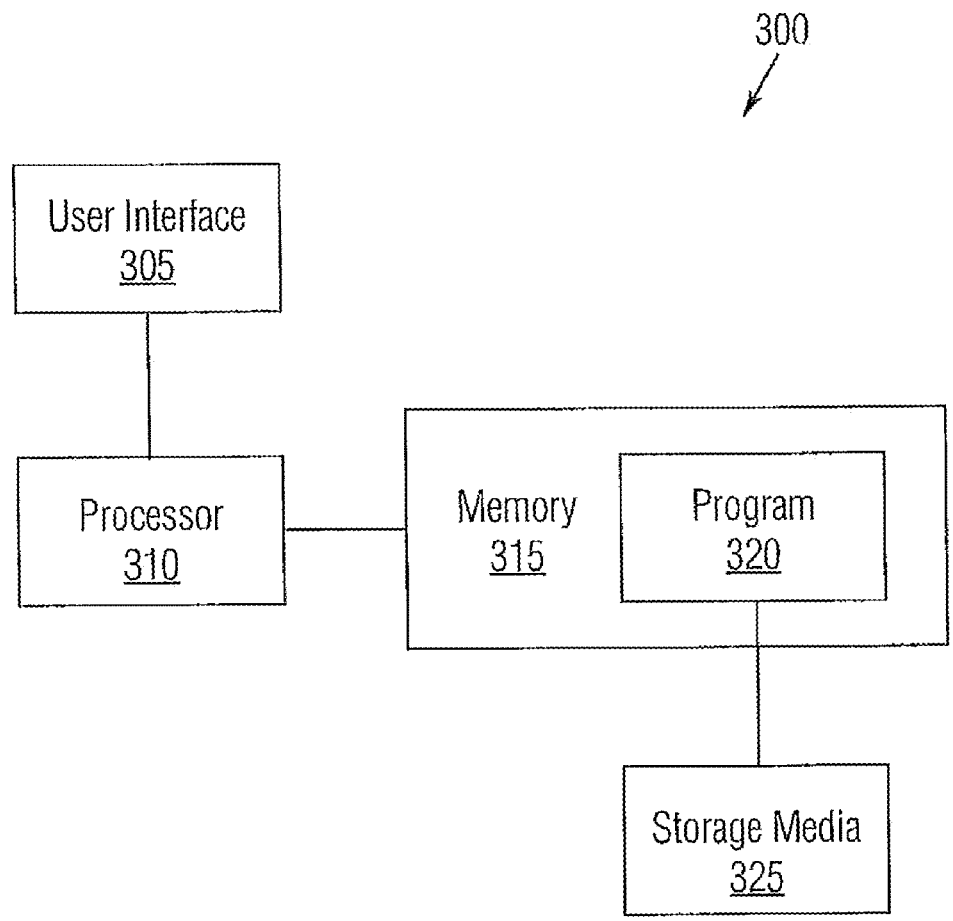
FIG. 9 is a block diagram of a computer system configured to employ one ablation method of the present invention.

FIG. 9 is a block diagram of one computer system 300 configured for employment of method 100. System 300 includes a user interface 305, a processor 310, and a memory 315. System 300 may be implemented on a general purpose microcomputer, such as one of the members of the Sun® Microsystems family of computer systems, one of the members of the IBM® Personal Computer family, one of the members of the Apple® Computer family, or a myriad other conventional workstations. Although system 300 is represented herein as a standalone system, it is not limited to such, but instead can be coupled to other computer systems via a network (not shown).

Memory 315 is a memory for storing data and instructions suitable for controlling the operation of processor 310. An implementation of memory 315 would include a random access memory (RAM), a hard drive and a read only memory (ROM). One of the components stored in memory 315 is a program 320.

Program 320 includes instructions for controlling processor 310 to execute method 100. Program 320 may be implemented as a single module or as a plurality of modules that operate in cooperation with one another. Program 320 is contemplated as representing a software embodiment of the method described hereinabove.

User interface 305 includes an input device, such as a keyboard, touch screen, tablet, or speech recognition subsystem, for enabling a user to communicate information and command selections to processor 310. User interface 305 also includes an output device such as a display or a printer. In the case of a touch screen, the input and output functions are provided by the same structure. A cursor control such as a mouse, track-ball, or joy stick, allows the user to manipulate a cursor on the display for communicating additional information and command selections to processor 310.

While program 320 is indicated as already loaded into memory 315, it may be configured on a storage media 325 for subsequent loading into memory 315. Storage media 325 can be any conventional storage media such as a magnetic tape, an optical storage media, a compact disc, or a floppy disc. Alternatively, storage media 325 can be a random access memory, or other type of electronic storage, located on a remote storage system.

The methods described herein have been indicated in connection with flow diagrams that facilitate a description of the principal processes; however, certain blocks can be invoked in an arbitrary order, such as when the events drive the program flow such as in an object-oriented program. Accordingly, the flow diagram is to be understood as an example flow and that the blocks can be invoked in a different order than as illustrated.

It should be understood that various combination, alternatives and modifications of the present invention could be devised by those skilled in the art. The present invention is intended to embrace all such alternatives, modifications and variances that fall within the scope of the appended claims.

Although described in connection with cardiac ablation procedures, it should be clear that the instruments and systems of the present invention can be used for a variety of other procedures where treatment with radiant energy is desirable, including laparoscopic, endoluminal, perivisceral, endoscopic, thoracoscopic, intra-articular and hybrid approaches.

Use of ICG Dye for Visualization of Treated Tissue

In accordance with the present invention, an ICG dye composition is used for visualizing ablated tissue and allowing the ablated tissue to be visually distinguished from de-novo tissue.

A suitable and biologically sufficient amount of ICG dye is delivered to the patient either immediately prior to performing the ablation procedure; during the ablative procedure or immediately after the ablation procedure. The timing and time period for delivering the ICG dye is sufficient to allow the ICG dye to travel through the bloodstream to the ablation tissue site where the ICG dye binds to plasma proteins and permit visualization of the ablated tissue since the ablated tissue (a lesion) is visually distinguishable from de novo tissue (non-ablated tissue) as a result of the binding properties of the ICG dye.

Accordingly, after the ICG dye is injected into the patient's arm (e.g., through an IV) or is otherwise delivered into the patient, it travels through the bloodstream to the target tissue in less than 1 minute (e.g., in about 15 to 20 seconds). As discussed herein, one of the properties of the ICG dye is that it binds to blood plasma protein and therefore, any tissue that absorbs the ICG dye (e.g., ICG binds with blood plasma protein) is readily distinguishable from tissue that does not absorb the ICG dye due to the difference in observable fluorescence.

As is understood, ablated tissue is tissue which has undergone coagulative necrosis due to energy being applied to the tissue. Unlike, the surrounding de-novo tissue, the ablated tissue does not have blood flowing therein and therefore, the ICG dye bound to blood plasma protein is carried into the ablated tissue to a far lesser extent than it is carried into de novo tissue. The result is that the ablated tissue does not absorb the ICG dye and is thus marked by a lack of fluorescence.

Figure 10:
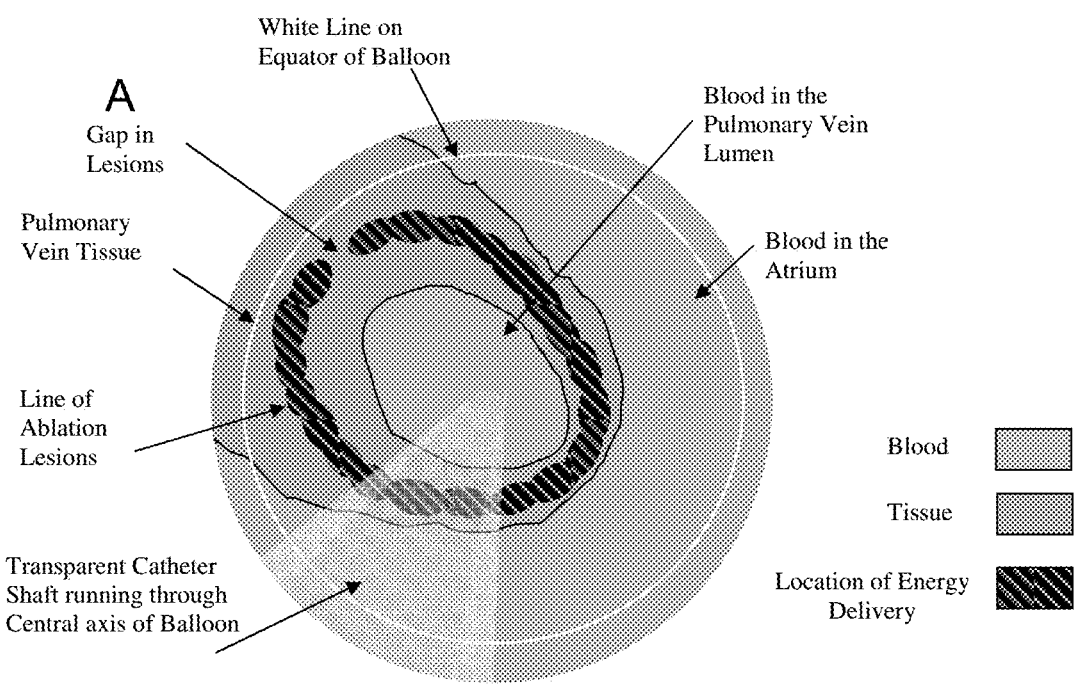
FIG. 10 is a representative view of a treatment site from along a longitudinal axis of a catheter.

FIG. 10 is a representative endoscopic view of a treatment site from along a longitudinal axis of the catheter. This view is preferably displayed on a display, such as a monitor and the ablated tissue is displayed in a visually distinguished manner relative to the de-novo (untreated) tissue. In particular and as a result of the use of the ICG dye, areas that contain blood (such as blood in the pulmonary vein lumen and blood in the atrium, etc.) are represented by high levels of fluorescence (which is graphically represented in the figure), while the area of the ablated tissue has a darker appearance due to a lack of ICG dye. In other words, the ablated tissue is easily distinguishable from the surrounding blood rich areas since the areas of ablated tissue lack the fluorescence that is exhibited in the blood rich areas.

In FIG. 10, the areas of blood/tissue are visually differentiated from the locations of the energy delivery (the formation of the lesions) by the use of cross-hatching. The catheter shaft and are also visually distinguished from the blood/tissue and the lesions (by cross-hatching). As discussed herein, in FIG. 10, the cross-hatched areas that denote blood/tissue are the areas of fluorescence when the appropriate energy is applied to the surgical site to cause the area to fluoresce The ablation system 10 described herein is modified by the inclusion of an excitation light that emits light at the proper excitation wavelength (e.g., about 805 nm) instead of the use of a white light that is used in other ablation procedures. The device also includes an imaging device, such as a camera or the like, which includes appropriate filters and is constructed to be able to detect and record near IR light near the peak of the ICG emission spectra (i.e., about 835 nm) on out to the limit of the ICG dye fluorescence spectrum (i.e. 880 nm) while filtering out all of the excitation light to allow the emitted fluorescence to be visible as shown in FIG. 10).

The principle of fluorescence imaging using ICG dye involves the following steps. The tissue of interest is illuminated at a selected excitation wavelength (about 750 nm to about 805 nm) while observing it at longer emission wavelengths (e.g., over 815 nm in the case of 805 nm excitation). Filters are preferably used as part of the imaging device to prevent mixing of the excitation (strong) and fluorescing (weak) rays to sum at a sensor or the like that is part of the overall imaging system. Even if the fluorescene is only a small fraction of the excitation intensity, a surprisingly good signal to noise ratio (SNR) is attached. A brightly fluorescing object (mostly blood and well perfused tissue) can be seen on a display. Without the use of filters, a weak fluorescene image cannot be seen among the strong reflection of the excitation light.

ICG fluoresces at about 800 nm and longer wavelengths. The exact shape of the observed spectra can depend somewhat on the chemical environment and physical conditions of the ICG molecules like temperature and ICG concentration as well as the absorption spectra of the tissue through which some of the emitted light must pass.

One of the advantageous properties of ICG is the fast binding to plasma proteins, especially lipoproteins, makes repeated intraoperational applications of ICG possible. The binding to plasma proteins does not alter the protein structures, which is one sign of nontoxicity. It is believed that ICG binds to the lipids of lipoprotein complexes ($\beta$-lipoprotein), and that the bind results in more intense fluorescence than ICG bound to for example, free cholesterol. Binding to protein proteins also shifts, slowly, taking several minutes, the absorption peak, at 780 nm, toward longer wavelengths, to 805 nm. It has been reported that absorption peak maximum was observed at 810 nm in the epidermal cell cultures, and at 805-810 nm in the human skin in vivo. The emission peak is also shifted similarly.

The Imaging System

The imaging system in accordance with the present invention includes an appropriate imaging device that is configured to monitor, in real time, the condition of the tissue at the surgical site and in particular, allow the physician to readily distinguish between ablated tissue and de novo tissue that has not been ablated. The imaging system allows the observed image to be displayed in real-time on a display and/or recorded and stored in memory.

An endoscope can be used to obtain an image of the ablated tissue as described herein. The endoscope is inserted into the body and positioned adjacent the area of interest. An instrument is then used in combination with the endoscope to provide energy at an appropriate wavelength to cause the ICG dye within the subject tissue to fluoresce so that the image can be obtained. Similarly, a second instrument can be used with the endoscope that permits the image of the fluorescing ICG dye within the tissue to be obtained. For example, an optical device is connected to a CCD camera can be used in conjunction with the endoscopic procedures of the present invention. The optical device and the CCD camera permits the physician to view the target tissue in the heart. When the imaging device is in the form of a CCD camera, the device includes software and equipment that effectively filters light (reflected light) of certain wavelength (s) and in particular, the imaging device can include one or more video chips and corresponding bandpass filters and/or other filter arrangements that allow the fluorescence emission of the ICG dye to be filtered out and then further processed. As is known, a traditional filter (e.g., a bandpass filter) can be tailored to a specific waveband of a certain width and is centered at a specific wavelength (i.e., the fluorescence emission).

Combined Visible and Fluorescence Images

According to one embodiment, fluorescence imaging can be done so that both visible or excitation and fluorescence images are displayed together as one image. The fluorescence image along may contain only a few details so that the visible image greatly helps to locate the fluorescing parts with the help of landmarks seen in the visible image. Typically, the fluorescence channel is shown, rendered, in colors like vivid green, having a striking color contrast to the visible image of tissues. The type of visualization is especially important in intraoperational use, where the fluorescing parts, like blood veins and healthy de novo tissue, should be recognized easily and immediately. Image registration software can then be used to combine the two images in proper alignment.

Review of Ablation Quality

The present invention thus allows the surgeon to view the formed ablation(s) (lesion) in real-time and to evaluate the quality of the formed ablation(s) to allow the surgeon to decide whether additional ablation treatment is needed. For example, if the surgeon views the display and notices that the formed ablation(s) includes a defect, such as a void (gap or break) along its length, or is otherwise not acceptable, then the surgeon can take corrective action.

A gap formed along the length of the lesion is readily recognizable since the area of the gap will exhibit fluorescence, while the other sections of the lesion lack fluorescence and appear dark. In FIG. 10, a gap (break) A is present in the lesion and is readily and immediately discoverable by the surgeon when viewing the display due to the fact that the area A (the gap area) fluoresces, while the lesion has a dark color on the display. Thus, holes/gaps located along the lesion are easily seen due to these areas appearing as fluorescent "hot spots" relative to the adjacent dark areas which represent the formed lesion(s).

After viewing the display, the surgeon can then further ablate the tissue to close off the gap or otherwise correct the formed ablation such that a complete ablation is formed as desired. The surgeon can then check the video display after performing such additional ablation to make sure that the lesion is complete as represented by a continuous dark segment (lack of fluorescence) on the video display. In other words, once corrective action is taken and these fluorescent "hot spots" are eliminated by ablating the tissue at such location, the "hot spots" will disappear. The vivid fluorescent colors that indicate the lack of ablated tissue and instead show areas of blood flow and de-novo tissue allow the surgeon in real-time to see deficiencies in the formed lesion (ablation) and take immediate corrective action, thereby ensuring that the lesion (ablation) is fully formed and will act to block electrical signals as desired.

U.S. patent application publication No. 2009/0326320 discloses other details of exemplary imaging systems and is hereby incorporated by reference in its entirety. It will be understood that one or more of the features disclosed in that document can be implemented in the imaging system of the present invention in that the imaging system can include more than one means for visualizing the surgical site and providing the user (surgeon) with helpful feedback and information concerning the quality of the lesion (i.e., whether the lesion is a continuous, uninterrupted structure, etc.).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed:

1. A method for distinguishing lesions from de novo tissue comprising the steps of:
    administering an ICG composition to the patient;
    forming one or more lesions at a surgical site;
    applying energy of a type and in an amount sufficient to cause ICG in the patient to fluoresce;
    obtaining an image of the tissue and lesion at the surgical site while the ICG fluoresces; and
    distinguishing the lesion from surrounding de novo tissue based on areas of fluorescence to allow a user to evaluate the quality of the lesion and to identify one or more breaks in the lesion that indicate an incomplete, non-continuous lesion is formed, each break in the lesion being identified as an area of fluorescence between parts of the lesion that define the break; and
    completing the lesion by ablating the tissue within the one or more breaks in the lesion until there is a lack of fluorescence between parts of the lesion that define the respective break.

2. The method of claim 1, wherein areas of the lesion are characterized by a lack of fluorescence.

3. The method of claim 1, wherein blood and the de novo tissue are characterized by areas of fluorescence.

4. The method of claim 1, wherein the step of applying energy comprises applying light that has a wavelength that is sufficient to cause the ICG to fluoresce.

5. The method of claim 1, wherein the image is in real-time.

6. The method of claim 1, further including the step of filtering light that is captured by an imaging device to limit the light to a wavelength at which ICG fluoresces.

7. The method of claim 1, further including the step of processing the filtered light to produce the image.

8. The method of claim 6, wherein the wavelength is about 805 nm.

9. The method of claim 1, wherein a common ablation instrument includes both an energy emitter for forming the lesion and a light beam for applying energy of the type and in the amount sufficient to cause the ICG composition to fluoresce.

10. The method of claim 1, wherein an image processor receives the images from endoscope of the surgical site and is configured to combine both visible light images of the surgical site which show anatomical landmarks with fluorescence images obtained with excitation light used to cause ICG in the patient to fluoresce and display the combined images as a single combined image, thereby allowing the one or more breaks in the lesion to be seen over the anatomical landmarks.

* * * * *